United States Patent
Luce

(12) 
(10) Patent No.: US 7,798,962 B2
(45) Date of Patent: Sep. 21, 2010

(54) METHOD AND APPARATUS FOR MEASURING CORNEAL RESISTANCE

(75) Inventor: David A. Luce, Clarence Center, NY (US)

(73) Assignee: Reichert, Inc., Depew, NY (US)

( * ) Notice: Subject to any disclaimer, the term of this patent is extended or adjusted under 35 U.S.C. 154(b) by 1154 days.

(21) Appl. No.: 11/222,132

(22) Filed: Sep. 8, 2005

(65) Prior Publication Data

US 2007/0055121 A1    Mar. 8, 2007

(51) Int. Cl.
*A61B 3/16* (2006.01)
*A61B 13/00* (2006.01)
*A61B 5/103* (2006.01)
*A61B 5/117* (2006.01)
*A61B 3/00* (2006.01)
*A61B 3/10* (2006.01)
*A61B 3/14* (2006.01)

(52) U.S. Cl. ............ 600/405; 600/398; 600/399; 600/400; 600/401; 600/402; 600/403; 600/404; 600/406; 600/558; 600/587; 351/200; 351/205; 351/206; 351/208; 351/209

(58) Field of Classification Search ............ 600/300, 600/372, 382, 383, 398, 399, 400, 401, 405, 600/406, 553, 558, 560, 561, 587; 128/920; 73/12.08; 351/200, 205, 206, 208, 209, 210
See application file for complete search history.

(56) References Cited

U.S. PATENT DOCUMENTS

| | | | |
|---|---|---|---|
| 6,419,631 B1 | 7/2002 | Luce | |
| 6,817,981 B2 | 11/2004 | Luce | |
| 6,875,175 B2 | 4/2005 | Luce | |
| 2004/0002640 A1* | 1/2004 | Luce | ............ 600/399 |
| 2004/0183998 A1 | 9/2004 | Luce | |

OTHER PUBLICATIONS

Zeimer Ophthalmic Systems AG, "Pascal Dynamic Contour Tonometer", Product Literature published Jan. 3, 2005.

* cited by examiner

*Primary Examiner*—Max Hindenburg
*Assistant Examiner*—Jeffrey G Hoekstra
(74) *Attorney, Agent, or Firm*—Hodgson Russ LLP

(57) ABSTRACT

A method and apparatus for measuring corneal resistance to deformation use an empirically derived function wherein an inward applanation pressure P1 and an outward applanation pressure P2 obtained during a corneal deformation cycle caused by a fluid pulse are separately weighted so as to minimize dependence of the calculated corneal resistance factor (CRF) on intraocular pressure. In one embodiment, the function is optimized, at least in part, to maximize statistical correlation between the calculated corneal resistance factor (CRF) and central corneal thickness.

7 Claims, 6 Drawing Sheets

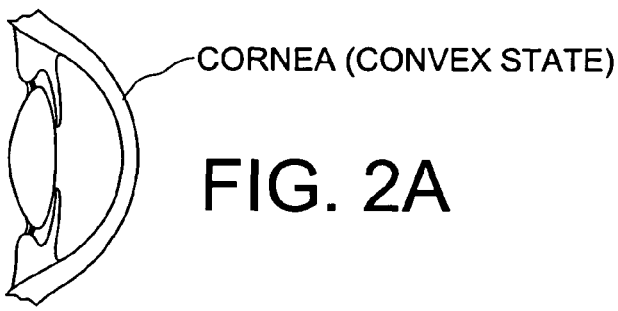
FIG. 2A — CORNEA (CONVEX STATE)
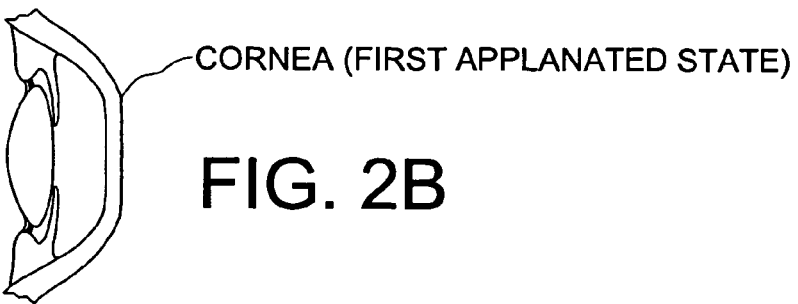
FIG. 2B — CORNEA (FIRST APPLANATED STATE)
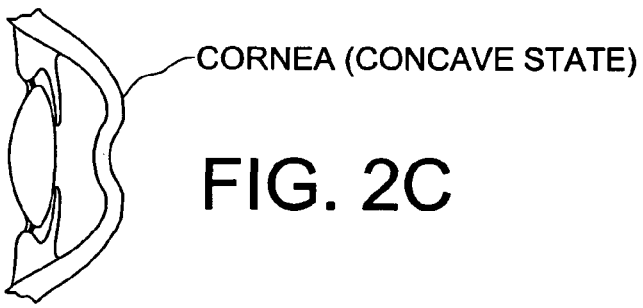
FIG. 2C — CORNEA (CONCAVE STATE)
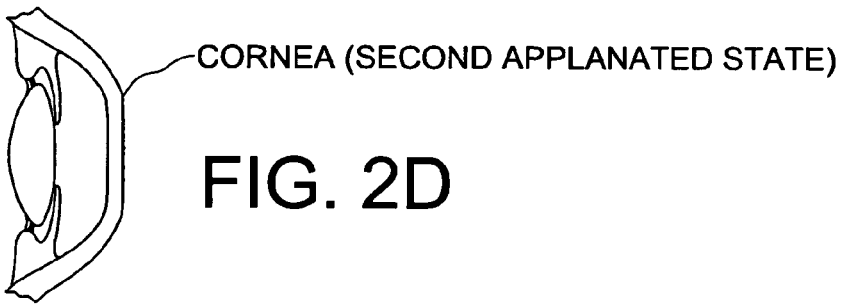
FIG. 2D — CORNEA (SECOND APPLANATED STATE)
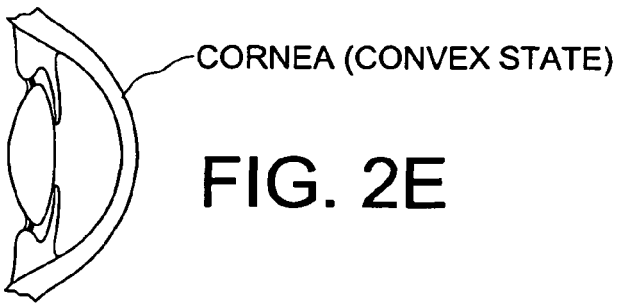
FIG. 2E — CORNEA (CONVEX STATE)

METHOD AND APPARATUS FOR MEASURING CORNEAL RESISTANCE

FIELD OF THE INVENTION

The invention relates generally to the field of ophthalmology, and more specifically to a method and apparatus for measuring corneal resistance to deformation.

BACKGROUND OF THE INVENTION

Tonometers for measuring IOP were originally developed as "contact" type instruments, meaning that a portion of the instrument is brought into contact with the cornea during the measurement procedure. A well-known instrument of this type is the Goldmann applanation tonometer (GAT) originally developed during the 1950s. The GAT measures the force required to flatten ("applanate") a known area of the cornea, and is used today as a standard against which other types of tonometers are compared to assess measurement accuracy.

Patient discomfort caused by contact tonometers such as the GAT led to the development of "non-contact" tonometers (NCTs) which operate by directing an air pulse at the patient's cornea to cause applanation. As the cornea is deformed by the fluid pulse, an optoelectronic system monitors the cornea by detecting corneally reflected light from a beam obliquely incident upon the cornea, and a peak detector signal occurs at the moment of applanation when the reflecting surface of the cornea is flat.

In state of the art NCTs, a pressure transducer measures the pump plenum pressure as the pulse is generated to provide a plenum pressure signal, whereby the plenum pressure at the moment applanation is achieved (indicated by a sharp peak in the applanation signal) can be determined. The plenum pressure at applanation is then converted to an IOP value in units of millimeters mercury (mmHg) using a linear regression equation stored during instrument clinical calibration relative to GAT as a reference. A primary index of an NCT's reliability is the standard deviation of differences $S_d$ of matched pairs of NCT and GAT clinical readings.

Current NCTs provide reasonably reliable IOP measurements, however recent studies indicate that corneal effects can have a significant impact on conventional NCT readings. This is not surprising, given that the cornea must be acted upon during the pressure measurement process and the air pulse must expend some of its energy "bending" the corneal tissue itself.

During a non-contact IOP measurement, the cornea is deformed from its original convex state through a first state of applanation to a slightly concave state, and is allowed to return from concavity through a second state of applanation to convexity as the air pulse decays. Indeed, a second peak corresponding to the second state of applanation is known to occur in the applanation signal. Thus, a first plenum pressure P1 coinciding with the first or inward applanation and a second plenum pressure P2 coinciding with the second or outward applanation are available from a single deformation cycle. U.S. Pat. No. 6,419,631 describes a non-contact tonometry method in which both P1 and P2 are used to calculate IOP.

The pair of pressures P1 and P2 have not been used solely for measuring IOP, but have also been evaluated in connection with measuring intrinsic properties of the cornea that are independent of IOP. U.S. Pat. No. 6,817,981 describes "corneal hysteresis" in the dynamic system, wherein the corneal hysteresis (CH) is defined as the pressure difference between the inward applanation pressure P1 and the outward applanation pressure P2. The corneal hysteresis is used as a second parameter that is evaluated in conjunction with reported IOP to assess the degree to which the reported IOP departs from an expected norm based on clinical data.

U.S. Patent Application Publication No. 2004-0183998 A1 describes a method for determining biomechanical characteristics of corneal tissue by evaluating corneal hysteresis in conjunction with a measurable geometric parameter of the cornea, for example central corneal thickness. The method is proposed as a LASIK screening tool.

While recent attention on corneal hysteresis has contributed valuable insight, it appears that corneal hysteresis provides an incomplete characterization of the cornea's biomechanical state. This is apparent from clinical data showing statistical correlation of corneal hysteresis with reported IOP and change in corneal hysteresis corresponding to induced change in IOP, both of which demonstrate that corneal hysteresis is not independent of reported IOP. Furthermore, clinical data show poor to moderate correlation of corneal hysteresis with central corneal thickness, whereas a more complete indicator of corneal properties should produce a stronger correlation with central corneal thickness.

SUMMARY OF THE INVENTION

It is thus an object of the present invention to provide a method and apparatus for measuring corneal resistance to deformation to provide a "corneal resistance factor" ("CRF") that is somewhat analogous to a "modulus of elasticity" for the cornea. A related object of the invention is to measure corneal resistance by evaluating measurement results already obtained part of an IOP measurement using existing NCT technology.

These and other objects are achieved by a method measuring corneal resistance to deformation generally comprising the steps of A) directing a fluid pulse at a cornea to cause reversible deformation of the cornea from an original state of convexity through a first state of applanation to a state of concavity, and back through a second state of applanation to the state of convexity; B) acquiring a first pressure value (P1) associated with the fluid pulse at a time of the first state of applanation and a second pressure value (P2) associated with the fluid pulse at a time of the second state of applanation; and C) calculating a corneal resistance factor (CRF) using a predetermined function of the first pressure value (P1) and the second pressure value (P2), wherein the function was empirically derived to minimize dependence of the calculated corneal resistance factor (CRF) on intraocular pressure. In an embodiment of the present invention, the empirically derived function is expressible as $$CRF = K_1 *(P1 - F*P2) + K_2$$

wherein $F \approx 0.7$, and $K_1$ and $K_2$ are constants.

The invention also comprises an ophthalmic instrument programmed to carry out the method using the empirically derived function, which may be stored in instrument memory.

The invention further provides a method of deriving a function for calculating a corneal resistance factor (CRF) indicative of corneal resistance to deformation, wherein the method generally comprises the steps of: A) referencing empirical data taken with respect to a plurality of eyes, the empirical data measuring a first pressure value (P1) associated with a first applanation of a cornea during a reversible deformation of the cornea and a second pressure value (P2) associated with a second applanation of the cornea during the reversible deformation, the first and second pressure vales (P1 and P2) being obtained both with and without induced alteration of intraocular pressure; B) choosing a form of the function wherein the first pressure value (P1) and the second pressure value (P2) are independently weighted variables; and C) determining relative weights of the first and second pressure values (P1 and P2) so as to maximize statistical correlation between the calculated corneal resistance factor (CRF) and central corneal thickness.

BRIEF DESCRIPTION OF THE DRAWINGS

The nature and mode of operation of the present invention will now be more fully described in the following detailed description taken with the accompanying drawing figures, in which:

FIGS. 2A through 2E are a sequential series of views showing stages of deformation of a cornea during measurement of IOP in accordance with a method of the present invention;

DETAILED DESCRIPTION OF THE INVENTION

Figure 1:
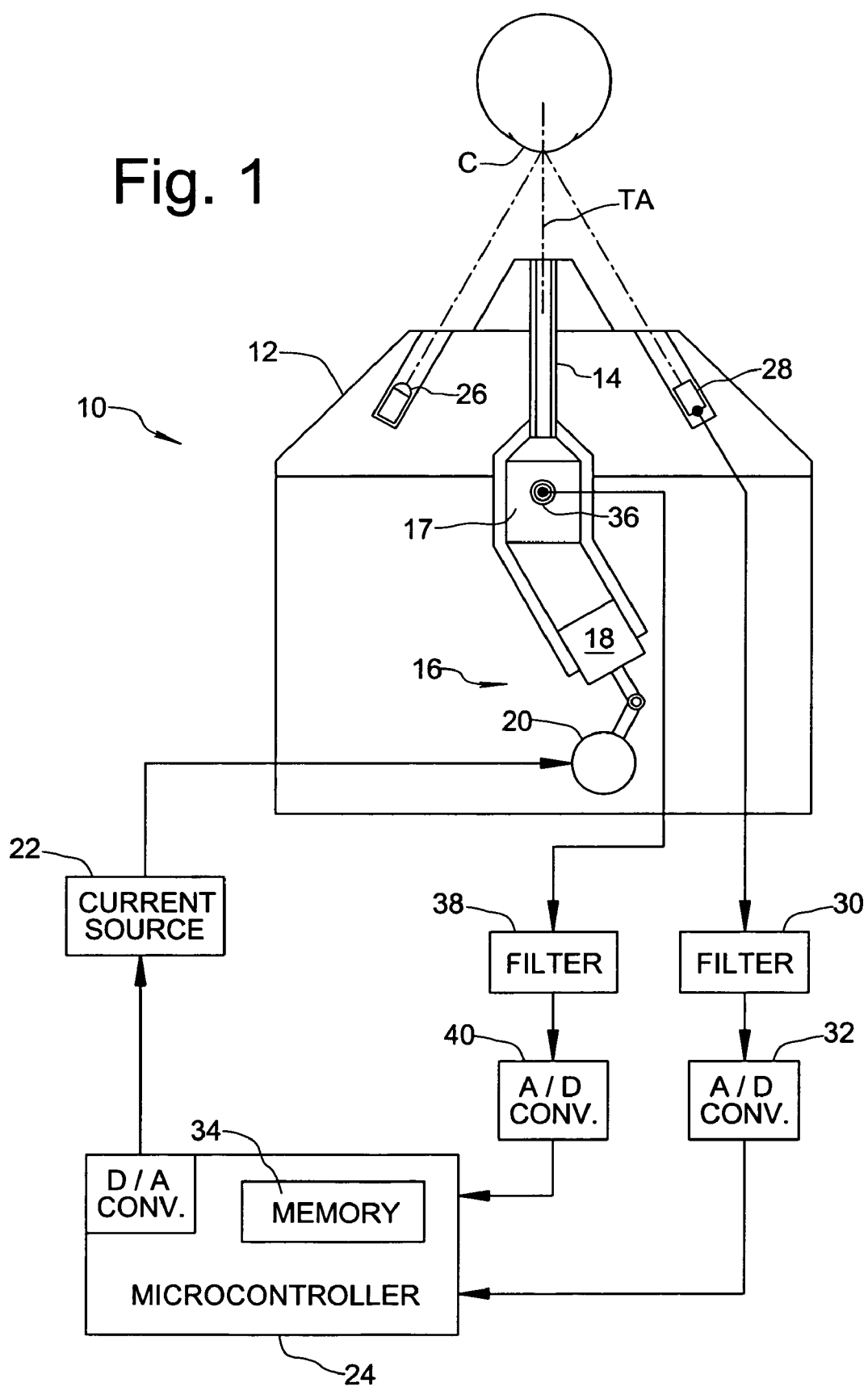
FIG. 1 is a schematic view of an NCT embodying the present invention.

FIG. 1 shows an ophthalmic instrument, namely a non-contact tonometer, 10 in schematic view. A test portion of NCT 10 is depicted as generally including a nosepiece 12 in which a fluid discharge tube 14 is fixed. The fluid discharge tube 14 defines a test axis TA that is aligned with a vertex of cornea C when measurement is carried out. The test portion of NCT 10 further includes a pump mechanism 16 having a plenum chamber 17 in flow communication with an entry end of fluid discharge tube 14, a piston 18 movable to compress fluid within plenum chamber 17, and a drive motor 20 connected to the piston. As will be familiar to persons skilled in the art of non-contact tonometry, the pump mechanism 16 is operable to rapidly increase fluid pressure within plenum chamber 17, thereby generating a fluid pulse that is discharged from an exit end of fluid discharge tube 14 in the direction of cornea C to cause deformation of the cornea. In the depicted embodiment, motor 20 is energized by a current source 22 in response to a command signal from a microcontroller 24. As used herein, the term "microcontroller" means any integrated circuit that includes at least a central processing unit (CPU) and a memory. The memory preferably includes a non-volatile memory device for retaining stored information when power is turned off. Suitable non-contact tonometers for practicing the present invention include, but are not limited to, the AT-555 Non-Contact Tonometer and the Ocular Response Analyzer (ORA) manufactured by Reichert, Inc., assignee of the present application.

FIGS. 2A-2E show a corneal deformation cycle caused by the fluid pulse. FIG. 2A shows cornea C in its original and natural convex state. FIG. 2B shows cornea C in a first state of applanation as the cornea is pushed inwardly by the fluid pulse, and FIG. 2C shows cornea C in a concave state as the air pulse pushes the corneal tissue beyond its flattened state of FIG. 2B. The air pulse then decays and the cornea is allowed to pass through a second state of applanation, shown in FIG. 2D, as the cornea deforms in an outward direction to return to its original and natural convex state depicted again in FIG. 2E.

Figure 3:
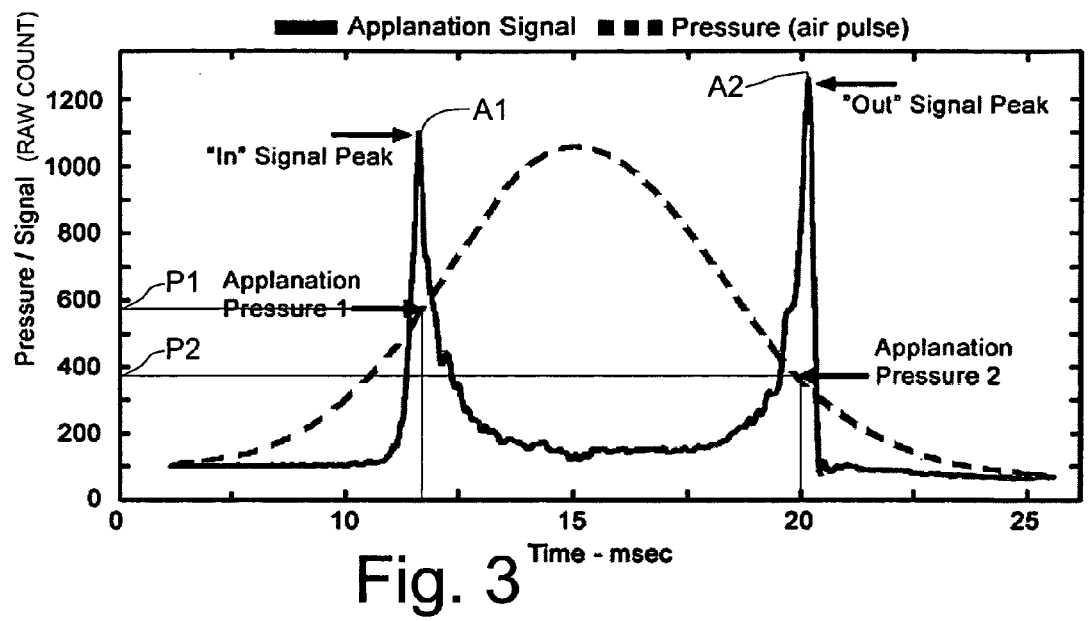
FIG. 3 is a graph showing an applanation signal and a plenum pressure signal during an NCT measurement in accordance with the present invention.

Corneal deformation may be monitored by an optoelectronic monitoring system such as that shown in FIG. 1, wherein a light source 26 is obliquely aimed at the cornea, and a photosensitive detector 28 is arranged on an opposite side of the test axis TA to receive corneally reflected light. As will be understood, when cornea C is convex (FIGS. 2A, 2E) or concave (FIG. 2C), a beam from light source 26 will become fanned out after reflection by the curved corneal surface and the signal generated by photosensitive detector 28 will be relatively weak. However, when cornea C is in an applanated state (FIGS. 2B and 2D), the light beam from light source 26 remains well-defined after reflection by the flattened corneal surface such that more light reaches photosensitive detector 28 and a peak signal is generated by the detector. The signal information generated by photosensitive detector 28 during the corneal deformation cycle, referred to herein as the "applanation signal," is processed by a filter 30, converted to digital form by analog-to-digital converter 32, and input to microcontroller 24 where it may be stored by memory 34. An applanation signal from a typical NCT measurement is plotted in FIG. 3, and includes a pair of well-defined signal peaks A1 and A2 corresponding to a first applanation event during inward deformation of cornea C (see FIG. 2B) and a second applanation event during outward deformation of cornea C (see FIG. 2D), respectively.

The pressure within plenum chamber 17 is also monitored during the corneal deformation cycle. In the embodiment shown, a pressure sensor 36 is positioned in plenum chamber 17 near the entry end of fluid discharge tube 14 to generate signal information representative of the plenum pressure associated with the fluid pulse. The signal information generated by pressure sensor 36 is processed by a filter 38, converted to digital form by analog-to-digital converter 40, and input to microcontroller 24 where it may be stored by memory 34. A pressure signal from an NCT measurement according to the invention is plotted in FIG. 3, and is characterized by a Gaussian bell curve shape. It is preferable to adjust the parameters of pump mechanism 16 to provide a pressure signal that is at least approximately symmetrical about a moment in time and has a suitable spread, whereby a first pressure P1 coinciding with first applanation A1 and a second pressure P2 coinciding with second applanation A2 may be accurately determined by evaluating the applanation and pressure signals. For example, parameters that may be adjusted to optimize the shape of the pressure signal as a function of time include the weight of piston 18 and the time profile of the energizing current delivered by current source 22 to motor 20. Evaluation of the applanation signal and pressure signal is performed by microcontroller 24.

Thus, during a single corneal deformation cycle, two digital pressure values are obtained corresponding to the detected plenum pressure at the time of inward applanation (FIG. 2B) and at the time of outward applanation (FIG. 2D). For purposes of this specification, the first or inward pressure value is denoted P1, and the second or outward pressure value is denoted P2. The pressure values P1 and P2 are expressed in raw form as a digital "count" proportional to the amplitude of the pressure signal generated by pressure sensor 36.

Based on analysis of data from various clinical trials, it was observed that pressure values P1 and P2 respond independently to various factors such as central corneal thickness, surgical alteration of the cornea, and clinically induced changes in IOP. Therefore, in accordance with the present invention, an "optimum combination" of the two independent parameters P1 and P2 was sought to yield the best numerical value representing corneal resistance in the measurement system, a quantity referred to herein as the "corneal resistance factor" or "CRF".

More specifically, a function for calculating a CRF from pressure values P1 and P2 was empirically derived from clinical data, wherein the function was optimized so as to maximize correlation of CRF with central corneal thickness (CCT) in various populations. Alternatively, or in combination with maximizing correlation of CRF with CCT, the function may be optimized to minimize change in CRF associated with an induced change in IOP, and/or to maximize correlation of CRF with IOP measured by GAT. The function must also ensure that the calculated CRF is a significant indicator of corneal conditions such as keratoconus and Fuch's dystrophy, and that there is corresponding change in the calculated CRF following surgical alteration of the cornea. As used herein, the term "minimize" and its alternate forms are used in a broad sense to include reducing a parameter. Likewise, the term "maximize" and its alternate forms are used in a broad sense to include increasing a parameter.

In a current embodiment, clinical data comprising plenum pressure values P1 and P2 and central corneal thickness for various populations were evaluated to derive the function for calculating CRF. Data used in development of the present invention were obtained in a clinical study performed at the Wilmer Eye Institute at Johns Hopkins Hospital in Baltimore, Md. The study was performed using GAT and an NCT manufactured by Reichert, Inc., owner of the present application. Data were collected on 339 eyes ranging in GAT IOP reading from 3.0 mmHg to 57.3 mmHg. Two NCT measurements per eye and three GAT measurements per eye were taken with random right/left eye selection and random GAT-NCT sequence. The resulting data are provided in Table I appearing at the end of this Detailed Description.

The function for calculating IOP was assumed to be a linear combination of pressure values P1 and P2. Without loss of generality, the linear function for calculating CRF in units of millimeters mercury can be written $$CRF = K_1 * (P1 - F * P2) + K_2 \quad (1)$$

wherein "$K_1$" is a scale factor converting arbitrary digital "count" units to millimeters mercury, "$K_2$" is an offset term, and "F" is a factor weighting P2 relative to P1. As will be understood, scale factor $K_1$ is determined by properties of the NCT measurement apparatus that influence the pressure signal.

Figure 4:
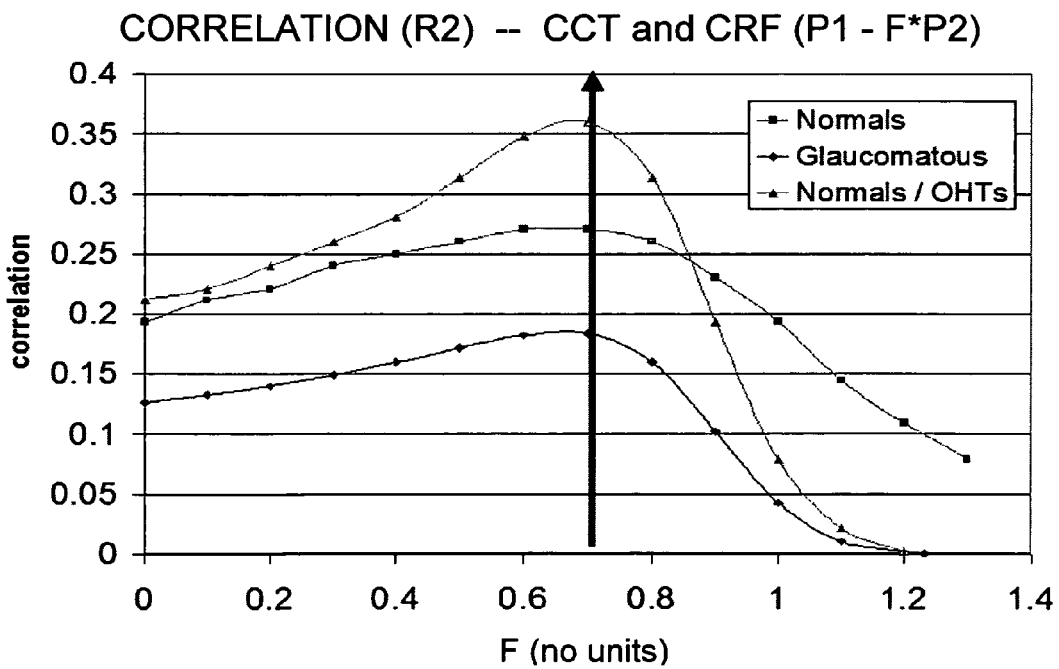
FIG. 4 is a graph of showing the behavior of statistical correlation between central corneal thickness and corneal resistance quantity P1−F*P2 as weighting factor F changes, for various populations of eyes.

Thus, the task of optimizing the above CRF function involves finding the value of weighting factor F that maximizes correlation of CRF with central corneal thickness in the clinical populations. Accordingly, the parenthetical term P1−F*P2 was plotted against central corneal thickness at incremental values of F, and statistical correlation $R^2$ between the two quantities was determined for the corresponding linear fit for each different value of F. Then, the resulting statistical correlation $R^2$ was plotted against weighting factor F as shown in FIG. 4. Three different correlation curves are presented in FIG. 4: a correlation curve for normal eyes, a correlation curve for glaucomatous eyes, and a correlation curve for normal and ocular hypertension (OHT) eyes. It is apparent from FIG. 4 that each of the three correlation curves reaches a maximum near F=0.7. Accordingly, the weighting factor F was empirically optimized to be 0.7, such that $$CRF = K_1 * (P1 - 0.7 * P2) + K_2 \quad (2)$$

It is emphasized that error exists with respect to every measurement, and thus the empirically derived value of weighting factor F may be expressed with an associated tolerance range. For present purposes, weighting factor F=0.7±0.05.

As mentioned above, the value of $K_1$ is specific to a given NCT, and therefore each NCT must be calibrated against a standard in order to provide a CRF value in standard units of millimeters mercury. One theoretical possibility for calibration is to determine $K_1$ for each specific instrument by calibrating each instrument against GAT. This may be done by measuring a plurality of eyes with GAT and measuring the same plurality of eyes with the instrument to be calibrated to obtain P1 and P2 raw count values for the same plurality of eyes. The data may then be evaluated by performing a normal linear regression of the average plenum pressure (P1+P2)/2 against GAT to find a scale factor relating pressure in arbitrary digital "count" units to an equivalent pressure in millimeters mercury, whereby pressures in instrument-specific "count" units may be converted to millimeters mercury. Mathematically, $$(P1+P2)/2 = m*GAT + b \quad (3)$$

where "m" is slope and "b" is offset (y-axis intercept). When converting a pressure difference such as corneal hysteresis (CH), defined as (P1−P2), the offset term "b" drops out and corneal hysteresis in millimeters mercury is given by $$CH = 1/m * (P1 - P2) \quad (4)$$

where the term "1/m" is the scale factor for converting raw count pressure to millimeters mercury. Thus, $$K_1 = 1/m \quad (5)$$

Figure 5:
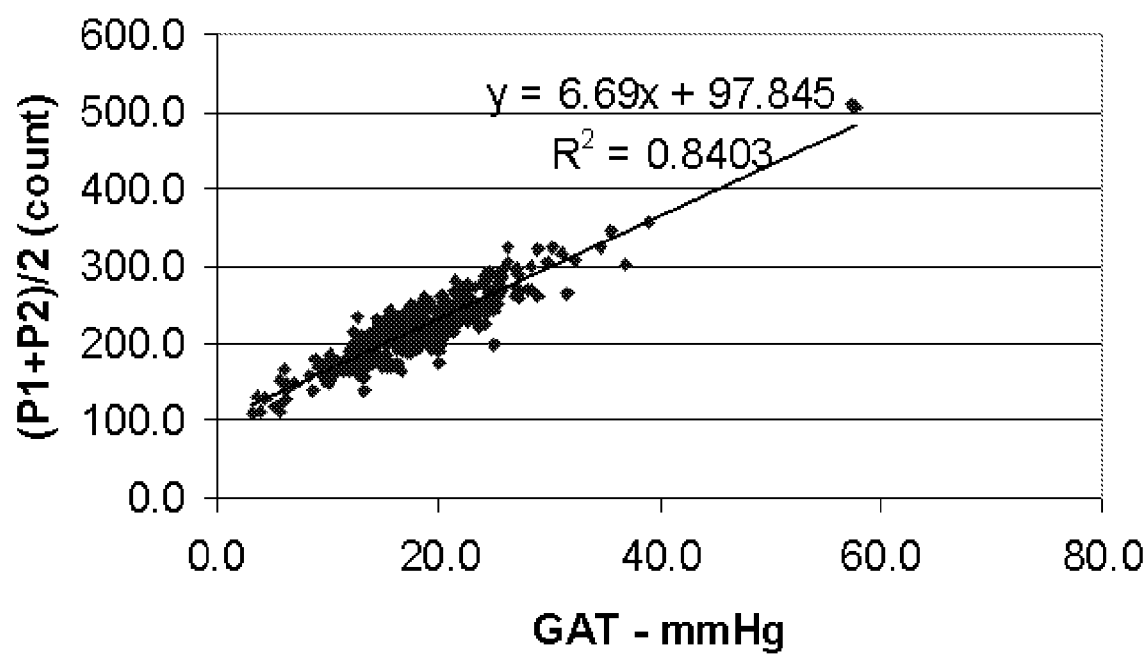
FIG. 5 is a graph of average plenum pressure versus GAT measurement values for a population of eyes measured with a master instrument.

Using the clinical data in Table I, the regression of (P1+P2)/2 against GAT yielded a slope of 6.69 as shown in FIG. 5. Therefore, $K_1$ for the master instrument used in the study was found to be 0.149.

A currently preferred derivation of $K_2$ will now be described. As will be appreciated, CRF in units of raw digital count is expressed $$CRF = P1 - 0.7 * P2 \quad (6)$$

which may be written $$CRF = 0.3 * P1 + 0.7 * (P1 - P2) = 0.3 * P1 + 0.7 * CH \quad (7)$$

where CH is in units of raw count. The first term 0.3*P1 may be thought of as a static resistance term that depends solely on the first or inward pressure P1, while the second term 0.7*CH may be thought of as a dynamic resistance term that depends on corneal hysteresis in the dynamic measurement. Consequently, it is helpful to choose $K_2$ in equation (2) such that the average CRF for a population of normal eyes will equal the average corneal hysteresis CH for a population of normal eyes. In this way, if the instrument is programmed to report both corneal hysteresis and CRF, the difference between reported CH and CRF provides meaningful insight into contributions from the static resistance term, for example when the cornea is relatively stiff due to higher-than-normal IOP. In a population of normal eyes, $$CRF_{avg} = CH_{avg} = 0.149 * (P1 - 0.7 * P2) + K_2 \quad (8)$$

In order to find $K_2$, it is necessary to input different values $K_2$ in equation (8) on an iterative basis, computing $CRF_{avg}$ for each new value of $K_2$, until the equation is satisfied. When this was done, the value of $K_2$ was determined to be −6.12. Unlike $K_1$, which is instrument specific, $K_2$ is a universal constant applicable to different instruments. Thus $$CRF=0.149*(P1-0.7*P2)-6.12 \qquad (9)$$

where CRF is in millimeters mercury.

Of course, it is highly impractical to calibrate each NCT intended for commercial sale in this manner. Instead, in order to calibrate each commercial NCT, a "master" NCT is calibrated as described above, and the calibrated master NCT is used as a reference standard for calibrating production NCTs intended for sale to customers. This latter step is preferably performed using a tonometer calibration tool and calibration methodology as described in commonly-owned U.S. Pat. No. 6,679,842. The tonometer calibration tool is used to determine an average value of P1 (baseline corrected count) provided by the master NCT for each of three different calibration pressure settings A (low), B (medium), and C (high) of the tonometer calibration tool. These plenum pressure calibration values associated with the master NCT are designated $P1_A^M$, $P1_B^M$, and $P1_C^M$, respectively. It is then necessary to determine an average value of P1 (baseline corrected count) provided by a subject production NCT for each of the three different calibration pressure settings A (low), B (medium), and C (high) of the tonometer calibration tool. These plenum pressure calibration values associated with the production NCT are designated $P1_A^P$, $P1_B^P$, and $P1_C^P$, respectively. Then, a linear regression of the production NCT pressure values versus the master NCT pressure values is performed:

$$(P1_A^P, P1_B^P, P1_C^P) \approx m_{ABC}*(P1_A^M, P1_B^M, P1_C^M)+b_{ABC} \qquad (10)$$

wherein $m_{ABC}$ and $b_{ABC}$ are calibration constants for the production NCT. The calibration constants $m_{ABC}$ and $b_{ABC}$ are used to convert the raw pressure values measured by a given production NCT into equivalent pressure values of the master NCT so that equation (9), derived for calculating CRF in the master NCT, is valid for calculating CRF in the production NCT. Accordingly, if the raw plenum pressure values measured by a production NCT are $P1_S$ and $P2_S$, then new calibration-converted plenum pressures $\overline{P1}_S$ and $\overline{P2}_S$ are calculated as follows:

$$\overline{P1}_S=(1/m_{ABC})*(P1_S-b_{ABC}) \qquad (11a)$$

$$\overline{P2}_S \leq (1/m_{ABC})*(P2_S-b_{ABC}) \qquad (11b)$$

The converted pressure values $\overline{P1}_S$ and $\overline{P2}_S$ may then be inputted to equation (9) to calculate CRF:

$$CRF=0.149*(\overline{P1}_S-0.7*\overline{P2}_S)-6.12 \qquad (12)$$

Thus, the parameters $K_1$ and $K_2$ derived for calculating IOP in the master NCT based on empirical data, and the calibration parameters $m_{ABC}$ and $b_{ABC}$ used for converting raw pressure values, are stored in memory 34 of each production instrument, along with programming code for performing the calculations set forth in equations (11a), (11b) and (12) above.

Figure 6:
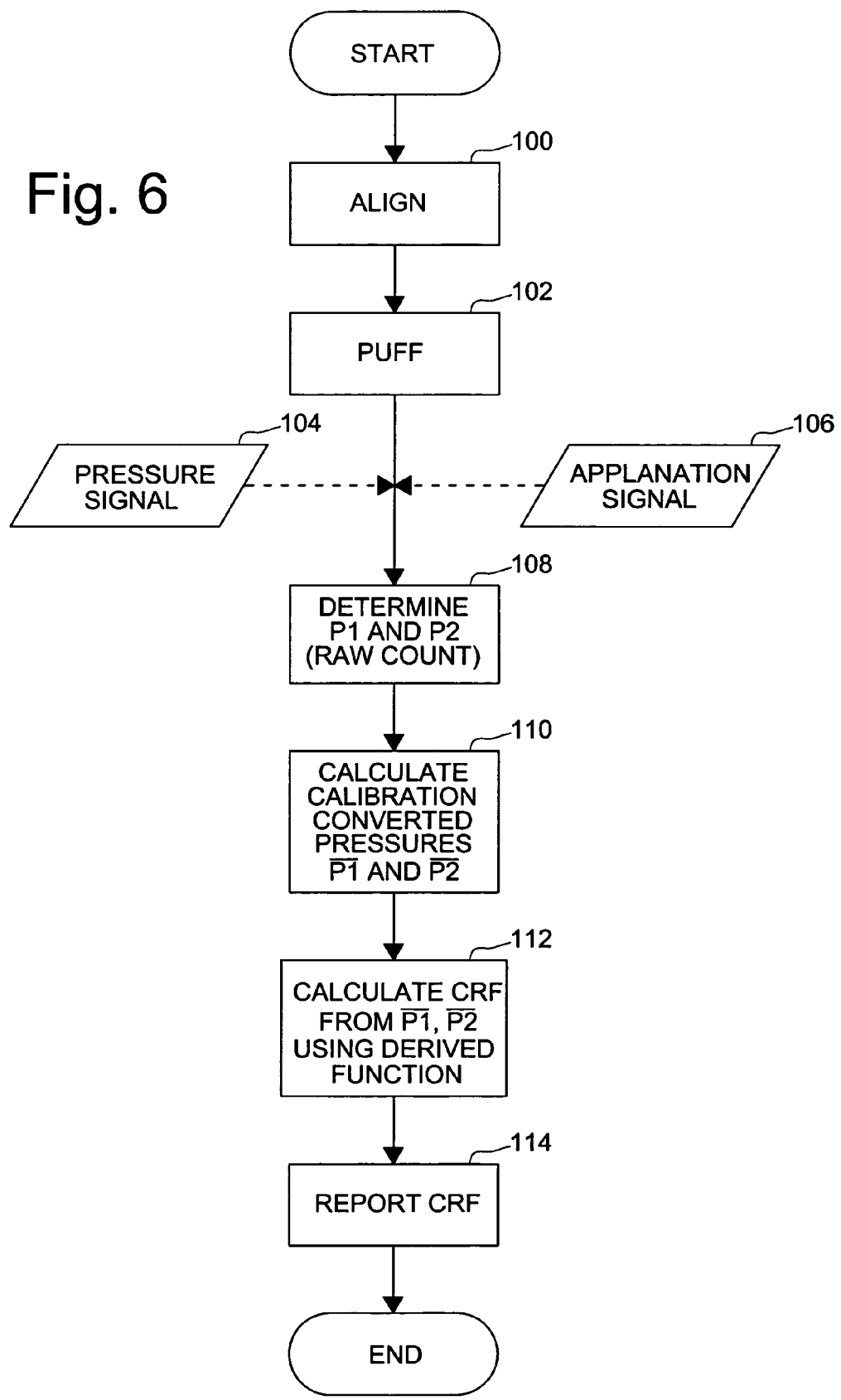
FIG. 6 is a flow chart illustrating a measurement process in accordance with an embodiment of the present invention.

FIG. 6 is a flow chart showing the measurement process carried out by an NCT calibrated and programmed in accordance with the present invention. The test axis TA of the NCT is aligned with the patient's eye in step 100, and a fluid pulse, for example an air puff, is directed at the cornea in step 102. Blocks 104 and 106 represent generation of a pressure signal and applanation signal as described above with respect to FIG. 3. In step 108, the pressure and applanation signals are digitized and the digitized signals are processed to determine pressure values P1 and P2. The pressure values P1 and P2 are adjusted in step 110 based on calibration of the instrument as described above to yield calibration corrected pressure values $\overline{P1}$ and $\overline{P2}$. In step 112 the calibration corrected pressure values $\overline{P1}$ and $\overline{P2}$ are input to the predetermined function for calculating CRF in millimeters mercury, which function may be stored in instrument memory, preferably non-volatile memory, during instrument calibration. Finally, the calculated CRF is reported in step 114, for example by displaying, printing, or audibly reporting the CRF value.

Figure 7:
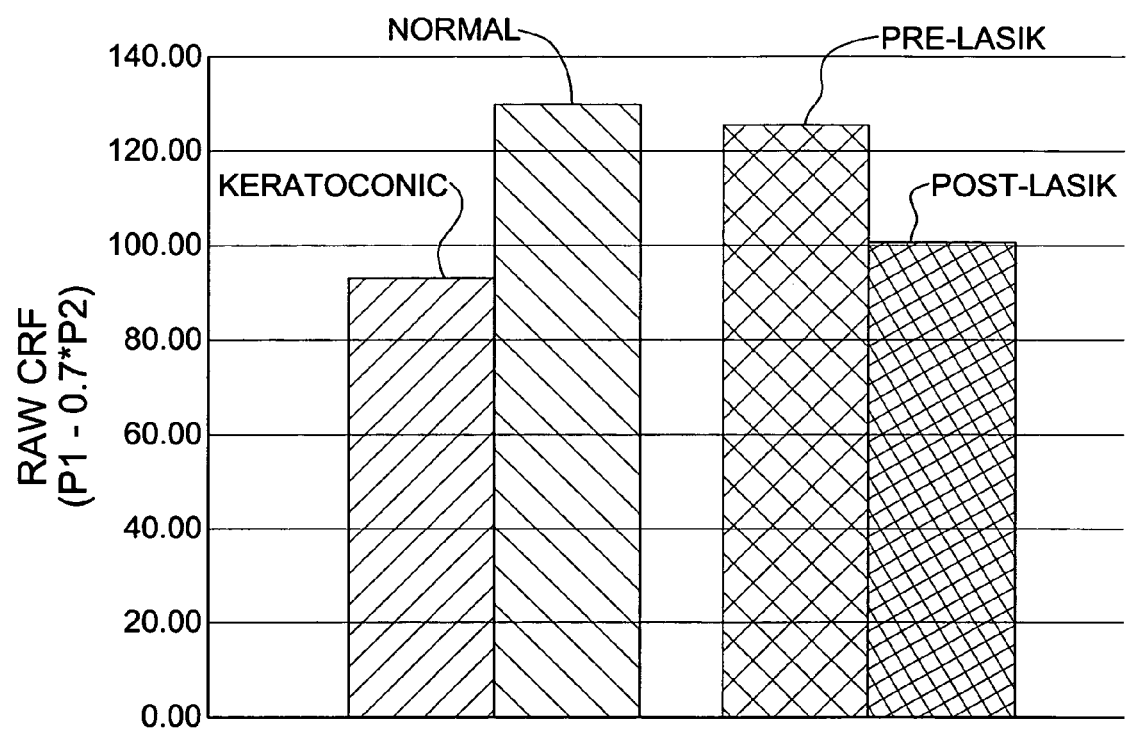
FIG. 7 is a graph providing a comparison between average CRF in a population of normal eyes and a population of keratoconic eyes, and a comparison between average CRF measured pre-LASIK and post-LASIK in a population of eyes.

FIG. 7 shows how average CRF for a population of normal eyes compares with average CRF for a population of keratoconic eyes, and also how average CRF for a population of eyes pre-LASIK surgery compares with average CRF for the same population of eyes post-LASIK surgery. FIG. 7 demonstrates that CRF calculated in accordance with the present invention is a significant indicator of keratoconus, and that there is corresponding change in the calculated CRF following surgical alteration of the cornea. These results agree with expected behaviors for a metric of corneal resistance.

As mentioned above, the function used to calculate the CRF may be optimized to minimize change in CRF associated with an induced change in IOP. For example, P1 and P2 may be measured in a population of eyes both with and without an administered pressure changing agent, such as Iopidine, and weighting factor F may be chosen such that the difference between CRF with Iopidine and CRF without Iopidine is minimized.

TABLE I

| GAT (mmHg) | CCT - (mm) | P1 - (count) | P2 - (count) | (P1 + P2)/2 (count) | P1 − P2 (count) | P1 − .7*P2 (count) | IOPG (mmHg) |
|---|---|---|---|---|---|---|---|
| 15.6 | 0.618 | 246.7 | 156.8 | 201.7 | 89.9 | 137.0 | 15.2 |
| 19.0 | 0.611 | 272.1 | 175.4 | 223.8 | 96.8 | 149.4 | 18.4 |
| 26.0 | 0.555 | 333.9 | 259.3 | 296.6 | 74.7 | 152.4 | 29.3 |
| 21.3 | 0.515 | 280.8 | 217.5 | 249.2 | 63.3 | 128.6 | 22.2 |
| 21.3 | 0.589 | 267.8 | 175.3 | 221.5 | 92.5 | 145.1 | 18.1 |
| 17.6 | 0.510 | 277.8 | 223.7 | 250.7 | 54.1 | 121.2 | 22.5 |
| 27.3 | 0.482 | 282.1 | 245.2 | 263.6 | 36.9 | 110.4 | 24.4 |
| 6.3 | 0.618 | 182.4 | 97.4 | 139.9 | 85.0 | 114.2 | 5.9 |
| 6.0 | 0.664 | 190.7 | 140.9 | 165.8 | 49.8 | 92.1 | 9.8 |
| 25.3 | 0.568 | 304.2 | 230.1 | 267.2 | 74.1 | 143.1 | 24.9 |
| 25.3 | 0.593 | 324.5 | 252.5 | 288.5 | 72.0 | 147.8 | 28.1 |
| 22.3 | 0.513 | 269.6 | 209.7 | 239.6 | 59.8 | 122.7 | 20.8 |
| 13.3 | 0.601 | 207.3 | 133.7 | 170.5 | 73.6 | 113.7 | 10.5 |
| 24.6 | 0.598 | 329.2 | 260.1 | 294.6 | 69.1 | 147.1 | 29.0 |
| 12.3 | 0.527 | 232.1 | 156.0 | 194.0 | 76.1 | 122.9 | 14.0 |

TABLE I-continued

| GAT (mmHg) | CCT - (mm) | P1 - (count) | P2 - (count) | (P1 + P2)/2 (count) | P1 − P2 (count) | P1 − .7*P2 (count) | IOPG (mmHg) |
|---|---|---|---|---|---|---|---|
| 20.3 | 0.585 | 238.0 | 158.3 | 198.2 | 79.7 | 127.2 | 14.6 |
| 18.3 | 0.531 | 245.1 | 188.0 | 216.6 | 57.0 | 113.5 | 17.4 |
| 24.6 | 0.533 | 307.5 | 223.9 | 265.7 | 83.6 | 150.8 | 24.7 |
| 18.6 | 0.589 | 267.9 | 216.2 | 242.1 | 51.7 | 116.6 | 21.2 |
| 12.0 | 0.485 | 195.5 | 144.7 | 170.1 | 50.8 | 94.2 | 10.4 |
| 19.6 | 0.550 | 238.5 | 162.2 | 200.4 | 76.2 | 124.9 | 15.0 |
| 9.3 | 0.556 | 202.0 | 137.8 | 169.9 | 64.2 | 105.5 | 10.4 |
| 19.3 | 0.619 | 250.6 | 186.6 | 218.6 | 64.0 | 120.0 | 17.7 |
| 8.3 | 0.578 | 194.6 | 120.1 | 157.3 | 74.6 | 110.6 | 8.5 |
| 10.6 | 0.719 | 193.2 | 139.1 | 166.2 | 54.1 | 95.9 | 9.8 |
| 17.6 | 0.544 | 277.1 | 203.1 | 240.1 | 74.0 | 134.9 | 20.9 |
| 15.3 | 0.509 | 217.2 | 176.0 | 196.6 | 41.2 | 94.0 | 14.4 |
| 13.3 | 0.556 | 222.4 | 179.8 | 201.1 | 42.6 | 96.5 | 15.1 |
| 10.3 | 0.477 | 214.5 | 158.2 | 186.4 | 56.3 | 103.8 | 12.9 |
| 11.3 | 0.562 | 213.1 | 142.0 | 177.6 | 71.0 | 113.6 | 11.5 |
| 13.0 | 0.576 | 246.4 | 162.8 | 204.6 | 83.6 | 132.4 | 15.6 |
| 24.3 | 0.516 | 260.1 | 217.1 | 238.6 | 43.0 | 108.1 | 20.7 |
| 27.0 | 0.548 | 299.8 | 243.9 | 271.9 | 55.9 | 129.0 | 25.6 |
| 15.3 | 0.591 | 247.1 | 158.9 | 203.0 | 88.2 | 135.8 | 15.3 |
| 31.3 | 0.568 | 335.5 | 295.3 | 315.4 | 40.2 | 128.8 | 32.1 |
| 28.0 | 0.542 | 301.2 | 238.9 | 270.0 | 62.3 | 134.0 | 25.4 |
| 18.6 | 0.506 | 236.5 | 186.5 | 211.5 | 50.1 | 106.0 | 16.6 |
| 12.6 | 0.564 | 198.9 | 122.4 | 160.7 | 76.5 | 113.2 | 9.0 |
| 18.0 | 0.570 | 258.7 | 198.3 | 228.5 | 60.4 | 119.9 | 19.1 |
| 9.3 | 0.502 | 218.4 | 126.9 | 172.6 | 91.4 | 129.5 | 10.8 |
| 15.3 | 0.575 | 272.8 | 190.2 | 231.5 | 82.6 | 139.7 | 19.6 |
| 18.3 | 0.551 | 254.7 | 174.9 | 214.8 | 79.8 | 132.3 | 17.1 |
| 10.0 | 0.536 | 214.7 | 126.6 | 170.7 | 88.1 | 126.1 | 10.5 |
| 14.6 | 0.498 | 211.7 | 166.6 | 189.1 | 45.1 | 95.1 | 13.3 |
| 18.0 | 0.548 | 223.1 | 170.5 | 196.8 | 52.6 | 103.7 | 14.4 |
| 24.6 | 0.575 | 283.4 | 200.6 | 242.0 | 82.8 | 143.0 | 21.2 |
| 18.0 | 0.489 | 248.9 | 178.8 | 213.9 | 70.1 | 123.7 | 17.0 |
| 22.3 | 0.586 | 291.2 | 191.8 | 241.5 | 99.4 | 156.9 | 21.1 |
| 18.3 | 0.582 | 263.5 | 187.5 | 225.5 | 76.1 | 132.3 | 18.7 |
| 24.0 | 0.552 | 291.5 | 263.2 | 277.3 | 28.3 | 107.2 | 26.5 |
| 10.6 | 0.509 | 201.0 | 148.2 | 174.6 | 52.8 | 97.2 | 11.1 |
| 19.3 | 0.590 | 286.6 | 222.0 | 254.3 | 64.6 | 131.2 | 23.0 |
| 20.3 | 0.565 | 259.2 | 198.4 | 228.8 | 60.8 | 120.3 | 19.2 |
| 17.3 | 0.656 | 279.9 | 210.5 | 245.2 | 69.3 | 132.5 | 21.6 |
| 15.3 | 0.539 | 232.2 | 158.2 | 195.2 | 74.0 | 121.4 | 14.2 |
| 16.6 | 0.641 | 245.5 | 189.7 | 217.6 | 55.8 | 112.7 | 17.5 |
| 11.3 | 0.498 | 201.8 | 133.7 | 167.7 | 68.1 | 108.2 | 10.1 |
| 15.6 | 0.571 | 247.8 | 171.3 | 209.5 | 76.5 | 127.9 | 16.3 |
| 18.6 | 0.556 | 252.2 | 166.7 | 209.4 | 85.5 | 135.5 | 16.3 |
| 12.6 | 0.543 | 203.0 | 132.9 | 167.9 | 70.0 | 109.9 | 10.1 |
| 22.3 | 0.607 | 323.2 | 219.7 | 271.4 | 103.4 | 169.3 | 25.6 |
| 15.3 | 0.543 | 273.1 | 188.2 | 230.7 | 84.9 | 141.4 | 19.5 |
| 13.0 | 0.574 | 247.3 | 172.2 | 209.7 | 75.1 | 126.8 | 16.3 |
| 22.3 | 0.656 | 302.2 | 231.4 | 266.8 | 70.8 | 140.2 | 24.9 |
| 12.0 | 0.525 | 213.0 | 143.3 | 178.1 | 69.6 | 112.6 | 11.6 |
| 25.0 | 0.618 | 280.2 | 206.0 | 243.1 | 74.2 | 136.0 | 21.3 |
| 13.3 | 0.559 | 176.3 | 104.3 | 140.3 | 72.0 | 103.3 | 6.0 |
| 19.3 | 0.564 | 236.2 | 163.7 | 200.0 | 72.5 | 121.6 | 14.9 |
| 23.6 | 0.588 | 252.4 | 188.1 | 220.3 | 64.2 | 120.7 | 17.9 |
| 11.3 | 0.542 | 194.9 | 131.2 | 163.0 | 63.8 | 103.1 | 9.4 |
| 18.3 | 0.570 | 251.4 | 182.9 | 217.2 | 68.5 | 123.4 | 17.5 |
| 21.0 | 0.612 | 272.2 | 204.3 | 238.3 | 67.9 | 129.2 | 20.6 |
| 21.3 | 0.564 | 292.9 | 241.1 | 267.0 | 51.9 | 124.2 | 24.9 |
| 18.0 | 0.521 | 254.0 | 189.2 | 221.6 | 64.8 | 121.5 | 18.1 |
| 25.3 | 0.619 | 298.9 | 253.2 | 276.1 | 45.7 | 121.7 | 26.3 |
| 18.0 | 0.541 | 259.3 | 170.9 | 215.1 | 88.4 | 139.6 | 17.1 |
| 15.6 | 0.527 | 239.6 | 174.0 | 206.8 | 65.6 | 117.8 | 15.9 |
| 22.0 | 0.563 | 271.4 | 191.0 | 231.2 | 80.4 | 137.7 | 19.6 |
| 20.3 | 0.602 | 310.3 | 212.9 | 261.6 | 97.4 | 161.3 | 24.1 |
| 11.6 | 0.581 | 216.3 | 144.7 | 180.5 | 71.6 | 115.0 | 12.0 |
| 25.3 | 0.512 | 285.2 | 238.9 | 262.0 | 46.4 | 118.0 | 24.2 |
| 14.3 | 0.554 | 239.5 | 165.0 | 202.2 | 74.5 | 124.0 | 15.2 |
| 5.6 | 0.571 | 157.9 | 83.4 | 120.7 | 74.6 | 99.6 | 3.0 |
| 16.6 | 0.609 | 274.5 | 200.4 | 237.5 | 74.1 | 134.2 | 20.5 |
| 19.0 | 0.521 | 254.7 | 174.7 | 214.7 | 79.9 | 132.4 | 17.1 |
| 13.3 | 0.548 | 228.5 | 159.2 | 193.8 | 69.3 | 117.0 | 14.0 |
| 20.6 | 0.541 | 254.8 | 200.7 | 227.7 | 54.1 | 114.3 | 19.0 |
| 14.3 | 0.600 | 235.3 | 181.0 | 208.2 | 54.3 | 108.6 | 16.1 |
| 15.0 | 0.593 | 261.0 | 183.9 | 222.5 | 77.0 | 132.2 | 18.3 |
| 18.6 | 0.547 | 262.4 | 198.8 | 230.6 | 63.6 | 123.2 | 19.5 |
| 18.6 | 0.639 | 292.9 | 225.9 | 259.4 | 66.9 | 134.7 | 23.8 |

TABLE I-continued

| GAT (mmHg) | CCT - (mm) | P1 - (count) | P2 - (count) | (P1 + P2)/2 (count) | P1 − P2 (count) | P1 − .7*P2 (count) | IOPG (mmHg) |
|---|---|---|---|---|---|---|---|
| 7.0 | 0.529 | 184.0 | 111.4 | 147.7 | 72.6 | 106.0 | 7.1 |
| 10.3 | 0.526 | 210.7 | 141.3 | 176.0 | 69.5 | 111.8 | 11.3 |
| 17.6 | 0.500 | 243.2 | 176.1 | 209.6 | 67.1 | 120.0 | 16.3 |
| 12.6 | 0.531 | 226.8 | 139.3 | 183.0 | 87.5 | 129.3 | 12.4 |
| 19.6 | 0.541 | 240.9 | 178.4 | 209.7 | 62.5 | 116.0 | 16.3 |
| 25.6 | 0.591 | 313.6 | 258.7 | 286.2 | 54.9 | 132.5 | 27.8 |
| 15.3 | 0.492 | 210.8 | 162.7 | 186.8 | 48.1 | 96.9 | 12.9 |
| 26.3 | 0.604 | 339.3 | 269.3 | 304.3 | 70.0 | 150.7 | 30.5 |
| 18.6 | 0.508 | 249.9 | 189.4 | 219.7 | 60.5 | 117.3 | 17.8 |
| 6.3 | 0.493 | 164.5 | 93.7 | 129.1 | 70.8 | 98.9 | 4.3 |
| 16.6 | 0.585 | 258.9 | 188.9 | 223.9 | 70.0 | 126.7 | 18.5 |
| 19.0 | 0.522 | 232.8 | 200.4 | 216.6 | 32.4 | 92.5 | 17.4 |
| 15.0 | 0.481 | 233.3 | 174.0 | 203.6 | 59.2 | 111.5 | 15.4 |
| 12.0 | 0.561 | 228.4 | 155.0 | 191.7 | 73.4 | 119.9 | 13.7 |
| 22.0 | 0.566 | 276.6 | 217.5 | 247.1 | 59.2 | 124.4 | 21.9 |
| 24.3 | 0.538 | 261.3 | 191.5 | 226.4 | 69.8 | 127.2 | 18.8 |
| 16.0 | 0.554 | 236.9 | 175.8 | 206.4 | 61.1 | 113.9 | 15.8 |
| 17.6 | 0.543 | 282.6 | 217.3 | 249.9 | 65.3 | 130.5 | 22.4 |
| 18.0 | 0.541 | 237.0 | 179.6 | 208.3 | 57.3 | 111.2 | 16.1 |
| 15.0 | 0.493 | 242.1 | 175.3 | 208.7 | 66.8 | 119.4 | 16.2 |
| 17.0 | 0.616 | 263.1 | 186.6 | 224.8 | 76.5 | 132.5 | 18.6 |
| 28.3 | 0.534 | 294.3 | 247.0 | 270.6 | 47.3 | 121.4 | 25.5 |
| 18.3 | 0.575 | 265.5 | 196.0 | 230.7 | 69.5 | 128.3 | 19.5 |
| 21.0 | 0.499 | 269.1 | 217.6 | 243.3 | 51.5 | 116.8 | 21.4 |
| 21.3 | 0.591 | 266.8 | 206.7 | 236.8 | 60.2 | 122.2 | 20.4 |
| 17.3 | 0.478 | 250.5 | 178.9 | 214.7 | 71.6 | 125.2 | 17.1 |
| 10.3 | 0.575 | 200.4 | 136.3 | 168.3 | 64.2 | 105.0 | 10.2 |
| 20.0 | 0.651 | 245.7 | 162.0 | 203.8 | 83.7 | 132.3 | 15.5 |
| 13.3 | 0.499 | 207.0 | 149.3 | 178.1 | 57.7 | 102.5 | 11.6 |
| 18.0 | 0.535 | 255.4 | 184.6 | 220.0 | 70.8 | 126.2 | 17.9 |
| 17.0 | 0.576 | 263.9 | 179.8 | 221.9 | 84.1 | 138.0 | 18.2 |
| 16.6 | 0.594 | 250.7 | 170.1 | 210.4 | 80.6 | 131.7 | 16.5 |
| 20.6 | 0.594 | 288.7 | 216.3 | 252.5 | 72.4 | 137.3 | 22.7 |
| 5.3 | 0.523 | 145.8 | 88.1 | 116.9 | 57.7 | 84.1 | 2.5 |
| 18.0 | 0.557 | 254.9 | 193.8 | 224.3 | 61.0 | 119.2 | 18.5 |
| 4.3 | 0.539 | 163.6 | 94.6 | 129.1 | 69.1 | 97.4 | 4.3 |
| 3.6 | 0.559 | 177.3 | 85.6 | 131.4 | 91.6 | 117.3 | 4.6 |
| 23.0 | 0.563 | 304.3 | 216.6 | 260.4 | 87.7 | 152.7 | 23.9 |
| 12.6 | 0.499 | 212.9 | 139.5 | 176.2 | 73.4 | 115.2 | 11.3 |
| 20.3 | 0.499 | 242.1 | 200.7 | 221.4 | 41.4 | 101.6 | 18.1 |
| 22.3 | 0.628 | 304.3 | 236.5 | 270.4 | 67.8 | 138.7 | 25.4 |
| 27.3 | 0.526 | 289.3 | 228.9 | 259.1 | 60.4 | 129.1 | 23.7 |
| 14.0 | 0.588 | 235.8 | 156.0 | 195.9 | 79.9 | 126.7 | 14.3 |
| 16.0 | 0.570 | 247.4 | 180.2 | 213.8 | 67.2 | 121.2 | 17.0 |
| 17.3 | 0.535 | 258.6 | 193.7 | 226.2 | 64.8 | 123.0 | 18.8 |
| 20.3 | 0.616 | 261.5 | 155.7 | 208.6 | 105.8 | 152.5 | 16.2 |
| 6.3 | 0.570 | 181.8 | 112.5 | 147.1 | 69.3 | 103.0 | 7.0 |
| 16.3 | 0.536 | 236.0 | 166.5 | 201.3 | 69.6 | 119.5 | 15.1 |
| 18.0 | 0.568 | 240.1 | 168.2 | 204.2 | 71.9 | 122.3 | 15.5 |
| 13.0 | 0.518 | 219.7 | 148.7 | 184.2 | 71.0 | 115.6 | 12.5 |
| 22.6 | 0.571 | 287.6 | 255.3 | 271.4 | 32.3 | 108.9 | 25.6 |
| 9.0 | 0.544 | 210.1 | 148.9 | 179.5 | 61.2 | 105.9 | 11.8 |
| 12.3 | 0.505 | 195.1 | 137.6 | 166.4 | 57.5 | 98.8 | 9.9 |
| 26.3 | 0.649 | 369.0 | 281.3 | 325.2 | 87.7 | 172.1 | 33.6 |
| 17.6 | 0.560 | 242.8 | 168.5 | 205.6 | 74.2 | 124.8 | 15.7 |
| 13.3 | 0.530 | 208.6 | 141.1 | 174.8 | 67.5 | 109.8 | 11.1 |
| 20.6 | 0.600 | 265.0 | 180.3 | 222.6 | 84.7 | 138.8 | 18.3 |
| 12.0 | 0.588 | 220.4 | 131.9 | 176.2 | 88.5 | 128.1 | 11.3 |
| 20.3 | 0.557 | 244.5 | 180.8 | 212.7 | 63.7 | 118.0 | 16.8 |
| 10.6 | 0.565 | 200.3 | 118.3 | 159.3 | 82.0 | 117.5 | 8.8 |
| 16.3 | 0.525 | 237.7 | 177.2 | 207.4 | 60.5 | 113.6 | 16.0 |
| 57.6 | 0.607 | 518.6 | 495.3 | 507.0 | 23.3 | 171.9 | 60.8 |
| 25.3 | 0.558 | 290.0 | 209.6 | 249.8 | 80.4 | 143.3 | 22.3 |
| 21.3 | 0.561 | 271.1 | 189.7 | 230.4 | 81.4 | 138.3 | 19.4 |
| 15.6 | 0.586 | 241.4 | 165.9 | 203.6 | 75.5 | 125.3 | 15.4 |
| 17.3 | 0.503 | 237.6 | 178.0 | 207.8 | 59.6 | 113.0 | 16.1 |
| 16.6 | 0.513 | 203.1 | 124.2 | 163.6 | 78.9 | 116.1 | 9.5 |
| 21.0 | 0.545 | 283.4 | 215.3 | 249.3 | 68.1 | 132.6 | 22.3 |
| 15.6 | 0.591 | 245.9 | 165.2 | 205.6 | 80.8 | 130.3 | 15.7 |
| 20.3 | 0.541 | 261.5 | 203.8 | 232.7 | 57.6 | 118.8 | 19.8 |
| 17.3 | 0.528 | 225.8 | 159.5 | 192.7 | 66.3 | 114.2 | 13.8 |
| 17.0 | 0.553 | 271.0 | 188.9 | 230.0 | 82.0 | 138.7 | 19.4 |
| 16.0 | 0.477 | 199.6 | 143.7 | 171.7 | 55.9 | 99.0 | 10.7 |
| 15.3 | 0.635 | 250.0 | 193.5 | 221.8 | 56.4 | 114.5 | 18.1 |
| 15.3 | 0.476 | 207.2 | 153.0 | 180.1 | 54.1 | 100.1 | 11.9 |
| 12.0 | 0.575 | 187.4 | 140.7 | 164.0 | 46.7 | 88.9 | 9.5 |

TABLE I-continued

| GAT (mmHg) | CCT - (mm) | P1 - (count) | P2 - (count) | (P1 + P2)/2 (count) | P1 − P2 (count) | P1 − .7*P2 (count) | IOPG (mmHg) |
|---|---|---|---|---|---|---|---|
| 27.3 | 0.603 | 323.1 | 257.2 | 290.1 | 65.9 | 143.1 | 28.4 |
| 24.6 | 0.607 | 306.7 | 266.6 | 286.7 | 40.0 | 120.0 | 27.8 |
| 28.3 | 0.594 | 327.8 | 274.5 | 301.1 | 53.2 | 135.6 | 30.0 |
| 22.6 | 0.574 | 272.6 | 184.0 | 228.3 | 88.6 | 143.8 | 19.1 |
| 19.3 | 0.523 | 230.5 | 156.8 | 193.6 | 73.8 | 120.8 | 13.9 |
| 18.3 | 0.588 | 280.2 | 222.7 | 251.4 | 57.5 | 124.3 | 22.6 |
| 21.3 | 0.606 | 261.6 | 170.7 | 216.1 | 90.9 | 142.1 | 17.3 |
| 27.0 | 0.575 | 289.6 | 234.7 | 262.2 | 54.8 | 125.3 | 24.2 |
| 22.0 | 0.522 | 290.1 | 225.1 | 257.6 | 65.0 | 132.5 | 23.5 |
| 21.3 | 0.511 | 269.4 | 208.6 | 239.0 | 60.9 | 123.4 | 20.7 |
| 25.0 | 0.478 | 292.4 | 245.4 | 268.9 | 47.1 | 120.7 | 25.2 |
| 3.3 | 0.608 | 151.2 | 64.6 | 107.9 | 86.5 | 105.9 | 1.1 |
| 21.0 | 0.666 | 248.2 | 209.9 | 229.1 | 38.3 | 101.3 | 19.2 |
| 24.3 | 0.566 | 298.3 | 246.6 | 272.4 | 51.7 | 125.6 | 25.7 |
| 30.0 | 0.601 | 342.6 | 267.7 | 305.1 | 74.9 | 155.2 | 30.6 |
| 20.0 | 0.517 | 246.2 | 189.2 | 217.7 | 57.0 | 113.8 | 17.5 |
| 18.3 | 0.587 | 231.1 | 162.4 | 196.8 | 68.7 | 117.4 | 14.4 |
| 21.3 | 0.610 | 280.8 | 201.4 | 241.1 | 79.4 | 139.9 | 21.0 |
| 14.3 | 0.559 | 257.1 | 204.8 | 231.0 | 52.3 | 113.7 | 19.5 |
| 14.0 | 0.572 | 223.1 | 148.9 | 186.0 | 74.2 | 118.8 | 12.8 |
| 17.3 | 0.534 | 236.2 | 170.9 | 203.5 | 65.3 | 116.6 | 15.4 |
| 22.6 | 0.541 | 277.4 | 198.0 | 237.7 | 79.4 | 138.8 | 20.5 |
| 19.0 | 0.589 | 268.0 | 188.8 | 228.4 | 79.2 | 135.8 | 19.1 |
| 13.3 | 0.500 | 209.7 | 165.8 | 187.8 | 43.9 | 93.7 | 13.1 |
| 5.6 | 0.582 | 188.6 | 118.2 | 153.4 | 70.4 | 105.9 | 7.9 |
| 20.3 | 0.524 | 240.7 | 181.8 | 211.2 | 58.9 | 113.4 | 16.6 |
| 22.3 | 0.592 | 287.7 | 218.3 | 253.0 | 69.5 | 135.0 | 22.8 |
| 15.3 | 0.576 | 259.1 | 180.8 | 219.9 | 78.3 | 132.5 | 17.9 |
| 19.0 | 0.564 | 243.4 | 187.4 | 215.4 | 56.1 | 112.3 | 17.2 |
| 14.0 | 0.556 | 249.5 | 163.7 | 206.6 | 85.8 | 134.9 | 15.9 |
| 10.3 | 0.499 | 192.3 | 127.1 | 159.7 | 65.1 | 103.3 | 8.9 |
| 20.0 | 0.580 | 215.7 | 134.7 | 175.2 | 81.0 | 121.4 | 11.2 |
| 18.3 | 0.470 | 258.0 | 224.6 | 241.3 | 33.3 | 100.7 | 21.1 |
| 13.0 | 0.544 | 225.8 | 161.5 | 193.6 | 64.4 | 112.8 | 13.9 |
| 13.6 | 0.577 | 242.0 | 169.6 | 205.8 | 72.4 | 123.3 | 15.8 |
| 20.6 | 0.606 | 220.5 | 197.8 | 209.1 | 22.8 | 82.1 | 16.3 |
| 31.6 | 0.541 | 303.6 | 225.8 | 264.7 | 77.8 | 145.5 | 24.6 |
| 30.3 | 0.581 | 356.1 | 291.9 | 324.0 | 64.2 | 151.8 | 33.4 |
| 24.0 | 0.560 | 288.9 | 211.5 | 250.2 | 77.4 | 140.8 | 22.4 |
| 18.0 | 0.581 | 243.3 | 194.0 | 218.6 | 49.2 | 107.4 | 17.7 |
| 20.6 | 0.536 | 248.4 | 186.3 | 217.4 | 62.1 | 118.0 | 17.5 |
| 37.0 | 0.516 | 328.8 | 277.0 | 302.9 | 51.7 | 134.9 | 30.3 |
| 15.3 | 0.547 | 211.7 | 125.0 | 168.3 | 86.7 | 124.2 | 10.2 |
| 16.6 | 0.563 | 241.6 | 177.9 | 209.8 | 63.7 | 117.1 | 16.4 |
| 10.6 | 0.501 | 212.1 | 139.9 | 176.0 | 72.2 | 114.2 | 11.3 |
| 18.6 | 0.594 | 277.3 | 207.5 | 242.4 | 69.9 | 132.1 | 21.2 |
| 18.0 | 0.564 | 256.3 | 180.5 | 218.4 | 75.8 | 130.0 | 17.6 |
| 9.6 | 0.549 | 213.2 | 125.5 | 169.3 | 87.7 | 125.3 | 10.3 |
| 14.6 | 0.518 | 211.0 | 139.4 | 175.2 | 71.6 | 113.4 | 11.2 |
| 18.3 | 0.556 | 233.1 | 166.0 | 199.5 | 67.1 | 116.9 | 14.8 |
| 19.3 | 0.571 | 253.5 | 172.5 | 213.0 | 81.0 | 132.8 | 16.8 |
| 20.3 | 0.494 | 242.6 | 164.6 | 203.6 | 78.0 | 127.4 | 15.4 |
| 23.3 | 0.575 | 298.9 | 193.3 | 246.1 | 105.6 | 163.6 | 21.8 |
| 20.0 | 0.583 | 249.4 | 168.3 | 208.8 | 81.0 | 131.5 | 16.2 |
| 19.0 | 0.538 | 261.6 | 192.2 | 226.9 | 69.4 | 127.1 | 18.9 |
| 18.3 | 0.509 | 247.6 | 205.5 | 226.6 | 42.1 | 103.8 | 18.9 |
| 12.6 | 0.596 | 251.1 | 167.0 | 209.0 | 84.1 | 134.2 | 16.2 |
| 20.6 | 0.552 | 284.2 | 226.2 | 255.2 | 58.0 | 125.8 | 23.1 |
| 17.6 | 0.634 | 269.4 | 204.6 | 237.0 | 64.8 | 126.2 | 20.4 |
| 16.3 | 0.536 | 236.1 | 153.3 | 194.7 | 82.8 | 128.8 | 14.1 |
| 12.6 | 0.616 | 259.9 | 211.0 | 235.4 | 48.9 | 112.2 | 20.2 |
| 10.0 | 0.493 | 178.4 | 113.9 | 146.2 | 64.5 | 98.7 | 6.8 |
| 19.3 | 0.570 | 250.6 | 176.0 | 213.3 | 74.6 | 127.4 | 16.9 |
| 19.0 | 0.554 | 259.5 | 184.5 | 222.0 | 74.9 | 130.3 | 18.2 |
| 13.6 | 0.554 | 213.2 | 147.8 | 180.5 | 65.3 | 109.7 | 12.0 |
| 23.0 | 0.603 | 324.6 | 220.6 | 272.6 | 104.0 | 170.1 | 25.7 |
| 19.6 | 0.549 | 271.8 | 187.7 | 229.7 | 84.1 | 140.4 | 19.3 |
| 14.0 | 0.578 | 262.8 | 168.1 | 215.4 | 94.6 | 145.1 | 17.2 |
| 24.3 | 0.678 | 307.0 | 263.9 | 285.5 | 43.1 | 122.3 | 27.7 |
| 11.0 | 0.536 | 215.7 | 139.4 | 177.6 | 76.3 | 118.1 | 11.5 |
| 29.0 | 0.610 | 291.1 | 232.3 | 261.7 | 58.9 | 128.5 | 24.1 |
| 13.3 | 0.519 | 192.4 | 119.6 | 156.0 | 72.8 | 108.7 | 8.3 |
| 15.6 | 0.582 | 207.1 | 131.5 | 169.3 | 75.5 | 115.0 | 10.3 |
| 21.6 | 0.570 | 261.0 | 185.8 | 223.4 | 75.2 | 131.0 | 18.4 |
| 14.6 | 0.562 | 216.8 | 152.8 | 184.8 | 64.0 | 109.8 | 12.6 |
| 19.3 | 0.569 | 247.0 | 180.2 | 213.6 | 66.8 | 120.9 | 16.9 |

TABLE I-continued

| GAT (mmHg) | CCT - (mm) | P1 - (count) | P2 - (count) | (P1 + P2)/2 (count) | P1 − P2 (count) | P1 − .7*P2 (count) | IOPG (mmHg) |
|---|---|---|---|---|---|---|---|
| 22.0 | 0.627 | 298.4 | 226.4 | 262.4 | 72.0 | 139.9 | 24.2 |
| 18.3 | 0.536 | 305.7 | 191.2 | 248.5 | 114.5 | 171.9 | 22.1 |
| 20.6 | 0.523 | 268.5 | 215.4 | 242.0 | 53.1 | 117.7 | 21.2 |
| 22.6 | 0.616 | 288.6 | 249.7 | 269.1 | 38.9 | 113.8 | 25.2 |
| 20.0 | 0.539 | 239.4 | 155.9 | 197.6 | 83.5 | 130.2 | 14.5 |
| 16.3 | 0.539 | 230.8 | 162.3 | 196.6 | 68.5 | 117.2 | 14.4 |
| 25.0 | 0.560 | 239.1 | 158.8 | 199.0 | 80.3 | 127.9 | 14.7 |
| 22.6 | 0.617 | 326.7 | 219.2 | 273.0 | 107.4 | 173.2 | 25.8 |
| 16.6 | 0.599 | 277.5 | 188.9 | 233.2 | 88.6 | 145.3 | 19.9 |
| 19.6 | 0.526 | 223.0 | 167.4 | 195.2 | 55.5 | 105.8 | 14.2 |
| 14.3 | 0.544 | 242.1 | 173.2 | 207.7 | 68.9 | 120.8 | 16.0 |
| 20.0 | 0.557 | 275.3 | 207.5 | 241.4 | 67.8 | 130.1 | 21.1 |
| 9.6 | 0.621 | 205.4 | 117.9 | 161.7 | 87.5 | 122.9 | 9.2 |
| 19.0 | 0.525 | 247.6 | 155.3 | 201.5 | 92.3 | 138.9 | 15.1 |
| 14.6 | 0.558 | 226.9 | 150.2 | 188.5 | 76.7 | 121.8 | 13.2 |
| 22.6 | 0.522 | 276.4 | 206.3 | 241.3 | 70.1 | 132.0 | 21.1 |
| 15.6 | 0.596 | 239.6 | 179.7 | 209.6 | 59.8 | 113.8 | 16.3 |
| 15.3 | 0.596 | 262.4 | 179.2 | 220.8 | 83.2 | 137.0 | 18.0 |
| 34.6 | 0.539 | 345.8 | 305.2 | 325.5 | 40.6 | 132.1 | 33.7 |
| 21.6 | 0.599 | 314.8 | 247.2 | 281.0 | 67.6 | 141.8 | 27.0 |
| 10.0 | 0.515 | 211.5 | 143.6 | 177.6 | 67.9 | 111.0 | 11.5 |
| 14.6 | 0.499 | 247.4 | 188.7 | 218.1 | 58.7 | 115.3 | 17.6 |
| 18.3 | 0.532 | 263.1 | 191.2 | 227.2 | 71.9 | 129.3 | 19.0 |
| 18.6 | 0.527 | 247.5 | 175.1 | 211.3 | 72.4 | 125.0 | 16.6 |
| 32.3 | 0.593 | 343.3 | 274.9 | 309.1 | 68.4 | 150.9 | 31.2 |
| 17.6 | 0.513 | 214.4 | 162.6 | 188.5 | 51.8 | 100.6 | 13.2 |
| 24.3 | 0.601 | 307.7 | 241.7 | 274.7 | 66.1 | 138.6 | 26.1 |
| 16.6 | 0.500 | 238.2 | 174.2 | 206.2 | 64.0 | 116.3 | 15.8 |
| 16.3 | 0.477 | 200.0 | 148.0 | 174.0 | 52.0 | 96.4 | 11.0 |
| 15.0 | 0.574 | 270.4 | 173.9 | 222.2 | 96.5 | 148.6 | 18.2 |
| 16.6 | 0.513 | 223.9 | 158.7 | 191.3 | 65.1 | 112.8 | 13.6 |
| 16.0 | 0.494 | 258.9 | 196.1 | 227.5 | 62.8 | 121.6 | 19.0 |
| 17.0 | 0.563 | 268.6 | 186.7 | 227.6 | 81.9 | 137.9 | 19.0 |
| 23.6 | 0.567 | 269.4 | 205.5 | 237.4 | 63.9 | 125.5 | 20.5 |
| 18.6 | 0.523 | 260.7 | 182.9 | 221.8 | 77.8 | 132.7 | 18.2 |
| 11.3 | 0.526 | 206.3 | 137.8 | 172.1 | 68.5 | 109.8 | 10.7 |
| 20.6 | 0.547 | 280.3 | 209.3 | 244.8 | 71.0 | 133.8 | 21.6 |
| 21.6 | 0.560 | 258.3 | 199.1 | 228.7 | 59.2 | 118.9 | 19.2 |
| 14.3 | 0.490 | 229.1 | 175.1 | 202.1 | 54.0 | 106.5 | 15.2 |
| 14.3 | 0.592 | 258.5 | 182.5 | 220.5 | 76.1 | 130.8 | 18.0 |
| 23.3 | 0.533 | 270.2 | 187.0 | 228.6 | 83.2 | 139.3 | 19.2 |
| 18.3 | 0.572 | 252.2 | 173.9 | 213.1 | 78.3 | 130.5 | 16.9 |
| 20.0 | 0.504 | 246.0 | 193.7 | 219.9 | 52.3 | 110.4 | 17.9 |
| 21.3 | 0.573 | 283.9 | 211.7 | 247.8 | 72.2 | 135.7 | 22.0 |
| 17.0 | 0.476 | 240.1 | 164.2 | 202.2 | 75.9 | 125.2 | 15.2 |
| 39.0 | 0.566 | 377.8 | 338.3 | 358.1 | 39.5 | 141.0 | 38.5 |
| 15.0 | 0.506 | 206.0 | 134.6 | 170.3 | 71.4 | 111.8 | 10.5 |
| 19.3 | 0.534 | 254.5 | 188.3 | 221.4 | 66.2 | 122.7 | 18.1 |
| 15.6 | 0.576 | 281.4 | 202.0 | 241.7 | 79.4 | 140.0 | 21.1 |
| 21.6 | 0.611 | 301.2 | 238.2 | 269.7 | 63.0 | 134.5 | 25.3 |
| 19.6 | 0.609 | 272.5 | 207.9 | 240.2 | 64.6 | 127.0 | 20.9 |
| 24.6 | 0.516 | 269.2 | 214.8 | 242.0 | 54.4 | 118.9 | 21.2 |
| 17.6 | 0.562 | 259.6 | 185.8 | 222.7 | 73.8 | 129.5 | 18.3 |
| 20.0 | 0.546 | 255.8 | 196.2 | 226.0 | 59.6 | 118.5 | 18.8 |
| 17.3 | 0.544 | 260.5 | 171.8 | 216.1 | 88.7 | 140.3 | 17.3 |
| 22.0 | 0.557 | 289.8 | 203.2 | 246.5 | 86.7 | 147.6 | 21.8 |
| 13.6 | 0.513 | 215.8 | 142.4 | 179.1 | 73.4 | 116.1 | 11.8 |
| 13.6 | 0.486 | 196.6 | 138.9 | 167.7 | 57.7 | 99.4 | 10.1 |
| 29.0 | 0.624 | 348.8 | 295.2 | 322.0 | 53.7 | 142.2 | 33.1 |
| 25.6 | 0.542 | 309.6 | 255.2 | 282.4 | 54.4 | 130.9 | 27.2 |
| 16.0 | 0.581 | 243.0 | 178.5 | 210.8 | 64.5 | 118.0 | 16.5 |
| 12.3 | 0.592 | 249.6 | 179.0 | 214.3 | 70.6 | 124.3 | 17.0 |
| 21.0 | 0.534 | 264.2 | 208.6 | 236.4 | 55.6 | 118.2 | 20.3 |
| 19.0 | 0.611 | 261.1 | 167.9 | 214.5 | 93.2 | 143.5 | 17.1 |
| 8.6 | 0.582 | 176.5 | 100.9 | 138.7 | 75.5 | 105.8 | 5.7 |
| 16.6 | 0.528 | 242.5 | 175.5 | 209.0 | 67.0 | 119.6 | 16.2 |
| 18.0 | 0.573 | 228.8 | 158.1 | 193.4 | 70.6 | 118.1 | 13.9 |
| 18.3 | 0.518 | 241.2 | 179.8 | 210.5 | 61.4 | 115.3 | 16.5 |
| 23.3 | 0.566 | 310.2 | 236.8 | 273.5 | 73.5 | 144.5 | 25.9 |
| 9.6 | 0.526 | 184.4 | 127.9 | 156.2 | 56.5 | 94.9 | 8.3 |
| 5.6 | 0.379 | 140.0 | 84.5 | 112.2 | 55.5 | 80.9 | 1.8 |
| 22.6 | 0.651 | 304.5 | 247.4 | 275.9 | 57.1 | 131.3 | 26.2 |
| 4.0 | 0.543 | 152.3 | 69.0 | 110.7 | 83.4 | 104.1 | 1.5 |
| 13.0 | 0.525 | 223.1 | 163.4 | 193.2 | 59.6 | 108.7 | 13.9 |
| 21.3 | 0.577 | 268.3 | 181.9 | 225.1 | 86.4 | 141.0 | 18.6 |
| 20.3 | 0.546 | 235.4 | 181.3 | 208.4 | 54.1 | 108.5 | 16.1 |

TABLE I-continued

| GAT (mmHg) | CCT - (mm) | P1 - (count) | P2 - (count) | (P1 + P2)/2 (count) | P1 − P2 (count) | P1 − .7*P2 (count) | IOPG (mmHg) |
|---|---|---|---|---|---|---|---|
| 11.6 | 0.566 | 205.5 | 125.7 | 165.6 | 79.8 | 117.5 | 9.8 |
| 17.3 | 0.546 | 256.8 | 184.3 | 220.6 | 72.5 | 127.8 | 18.0 |
| 57.3 | 0.618 | 530.3 | 490.5 | 510.4 | 39.9 | 187.0 | 61.3 |
| 21.3 | 0.561 | 263.9 | 188.8 | 226.4 | 75.1 | 131.7 | 18.8 |
| 17.3 | 0.575 | 260.7 | 185.4 | 223.0 | 75.3 | 130.9 | 18.3 |
| 13.6 | 0.486 | 203.1 | 138.7 | 170.9 | 64.4 | 106.0 | 10.5 |
| 17.3 | 0.511 | 216.6 | 161.7 | 189.1 | 54.9 | 103.4 | 13.3 |
| 27.0 | 0.590 | 327.2 | 267.3 | 297.2 | 59.9 | 140.1 | 29.4 |
| 12.3 | 0.732 | 238.3 | 158.8 | 198.5 | 79.5 | 127.1 | 14.7 |
| 30.3 | 0.519 | 340.9 | 306.9 | 323.9 | 34.0 | 126.0 | 33.4 |
| 25.6 | 0.526 | 283.7 | 250.1 | 266.9 | 33.6 | 108.7 | 24.9 |
| 17.6 | 0.548 | 276.6 | 187.5 | 232.0 | 89.1 | 145.3 | 19.7 |
| 14.0 | 0.457 | 207.9 | 161.8 | 184.8 | 46.1 | 94.6 | 12.6 |
| 18.3 | 0.612 | 277.3 | 210.7 | 244.0 | 66.6 | 129.8 | 21.5 |
| 12.6 | 0.519 | 218.8 | 152.4 | 185.6 | 66.3 | 112.0 | 12.7 |
| 18.6 | 0.594 | 264.2 | 197.3 | 230.7 | 66.9 | 126.1 | 19.5 |
| 25.0 | 0.601 | 287.8 | 226.3 | 257.1 | 61.5 | 129.4 | 23.4 |
| 25.3 | 0.615 | 301.6 | 239.0 | 270.3 | 62.6 | 134.3 | 25.4 |
| 35.6 | 0.598 | 368.5 | 323.3 | 345.9 | 45.2 | 142.1 | 36.7 |
| 20.0 | 0.531 | 229.7 | 150.5 | 190.1 | 79.3 | 124.4 | 13.4 |

What is claimed is:

1. An ophthalmic instrument comprising:

a fluid pump including a plenum chamber;

a fluid discharge tube in communication with the pump for directing a fluid pulse at a cornea of a patient to cause reversible deformation of the cornea from an original state of convexity through a first state of applanation to a state of concavity, and back through a second state of applanation to the state of convexity;

an applanation detector providing an applanation signal indicating a time of the first state of applanation and a time of the second state of applanation;

a pressure sensor arranged to provide a pressure signal indicating fluid pressure in the plenum chamber as a function of time; and a programmable processor connected to the applanation detector and the pressure sensor, wherein the processor is programmed to evaluate the applanation signal and the pressure signal to provide a first pressure value (P1) coinciding with the first state of applanation and a second pressure value (P2) coinciding with the second state of applanation, and the processor is programmed with a predetermined function of the first pressure value (P1) and the second pressure value (P2) to calculate a corneal resistance factor (CRF) indicative of corneal resistance to deformation, wherein the predetermined function is empirically derived to minimize dependence of the calculated corneal resistance factor (CRF) on intraocular pressure, and wherein the predetermined function includes a static resistance term that depends solely on the first pressure value (P1) and a dynamic resistance term that depends on corneal hysteresis (CH) in the reversible deformation of the cornea, wherein corneal hysteresis (CH) is defined as a difference between the first pressure value (P1) and the second pressure value (P2); and means for reporting the calculated corneal resistance factor (CRF).

2. The ophthalmic instrument according to claim 1, further comprising a memory connected to the processor, wherein the memory stores the empirically derived function.

3. The ophthalmic instrument according to claim 2, wherein the function is optimized, wherein the optimization of the function includes maximization of statistical correlation between the calculated corneal resistance factor (CRF) and central corneal thickness.

4. The ophthalmic instrument according to claim 2, wherein the function is optimized, wherein the optimization of the function includes minimization of change in the calculated corneal resistance factor (CRF) between measurements made without induced alteration of intraocular pressure and measurements made with induced alteration of intraocular pressure.

5. The ophthalmic instrument according to claim 4, wherein the function is derived from empirical data, wherein the empirical data includes data measuring the first pressure value (P1) and the second pressure value (P2) both with and without induced alteration of intraocular pressure.

6. The ophthalmic instrument according to claim 2, wherein the predetermined function is a linear function.

7. The ophthalmic instrument according to claim 6, wherein the function is expressible as $$CRF = K_1 * (P1 - F * P2) + K_2$$

wherein $F \approx 0.7$, and $K_1$ and $K_2$ are constants.

* * * * *